United States Patent [19]
Kuettner et al.

[11] 4,042,457
[45] Aug. 16, 1977

[54] PREPARATION OF TISSUE INVASION INHIBITOR AND METHOD OF TREATMENT UTILIZING THE INHIBITOR

[75] Inventors: Klaus E. Kuettner, Chicago; Reuben Eisenstein, Lincolnwood, both of Ill.; Nino Sorgente, Los Angeles, Calif.

[73] Assignee: Rush-Presbyterian-St. Luke's Medical Center, Chicago, Ill.

[21] Appl. No.: 630,275

[22] Filed: Nov. 10, 1975

[51] Int. Cl.$^2$ .......................... C12B 3/00; C12K 9/00; A61K 35/12
[52] U.S. Cl. ..................................... 195/1.8; 195/1.7; 424/95
[58] Field of Search ..................... 195/1.7, 1.8; 424/95

[56] References Cited
PUBLICATIONS

Willmer-Cells and Tissues in Culture, vol. 1 (1965), pp. 44 and 573.

Primary Examiner—Sam Rosen
Attorney, Agent, or Firm—Fitch, Even, Tabin & Luedeka

[57] ABSTRACT

A composition of matter having activity as an inhibitor of cell proliferation is obtained by aqueous extraction of tissue having a high content of collagen and/or proteoglycans.

10 Claims, No Drawings

PREPARATION OF TISSUE INVASION INHIBITOR AND METHOD OF TREATMENT UTILIZING THE INHIBITOR

The present invention relates generally to a composition of matter having activity as an inhibitor of cell proliferation. More particularly, it relates to methods of preparing such composition, and to methods of inhibiting proliferation of cells utilizing such composition.

In accordance with the present invention, a substance having activity as an inhibitor of cell proliferation or, as it is sometimes referred to herein, an inhibitor of cell growth, is prepared by extractive methods from tissue having a high content of collagen and/or proteoglycans, and preferably from connective tissue. The extract may be treated so as to concentrate the inhibiting substance. The resultant concentrate has utility in inhibiting proliferation of cells, and particularly in inhibiting proliferation of fibroblasts and endothelial cells.

More particularly, in the preferred embodiment of the present invention, connective tissue is extracted with an aqueous extraction medium. A preferred extraction medium includes a solute which does not irreversibly denature proteins or proteoglycans. One such preferred extraction medium comprises a 1.0–3.0 M aqueous solution of guanidine hydrochloride.

Examples of connective tissue which may be used in the preferred embodiment of the present invention include cartilagenous and ligamentary tissues, vascular tissues, corneal tissues, dental tissues and dermal tissues. The connective tissue is placed in condition for extraction by mincing, comminuting, or otherwise treating it to increase the surface area of the tissue over that in its naturally-occurring condition. The conditioned tissue is then exposed to the aqueous extraction medium, with or without agitation, for a period of time sufficient to result in extraction of polypeptides and proteoglycans in substantial yield, or until equilibrium conditions are attained. Extraction is desirably effected at temperatures below room temperature, and preferably at approximately 5° C.

Following extraction, the aqueous extract is treated to concentrate the growth inhibiting substance contained therein. It is believed that the growth inhibiting substance of the present invention is present primarily in the fraction of the extract having a molecular weight of 50,000 or below. Accordingly, the extract may be treated so as to fractionate compounds having a molecular weight of 50,000 or less from those of higher molecular weight, by molecular sieve or ultrafiltration techniques, etc. or the like. The growth inhibiting substance of the present invention may be further concentrated by removal of water, as by lyophilization of the extract.

The growth inhibiting substance thus obtained has a marked inhibitory effect on the rate of proliferation of endothelial cells. It also inhibits proliferation of some fibroblasts, although inhibition of fibroblast growth is less marked than inhibition of growth of endothelial cells. In general, the growth inhibiting substance of the present invention is more effective against the proliferation of immature cells than of mature cells.

The extraction medium employed in the practice of the present invention may be any aqueous extraction medium, except that the extraction medium should not irreversibly denature the proteinaceous matter extracted from the connective tissue. An aqueous extraction medium containing a relatively high salt content, i.e., 1.0–3.0 M, is desirably used. A preferred extraction medium is a 1.0–3.0 M aqueous solution of guanidine hydrochloride.

If a high salt aqueous extraction medium is used, the salt should be removed from the extract, and this may be accomplished by dialysis, in accordance with known procedures.

The concentration of the growth inhibiting substance of the present invention in the connective tissue and in the aqueous extract is low. For example, it is necessary to extract several hundred grams of connective tissue in order to obtain a few milligrams of the lyophilized extract having a molecular weight of 50,000 or below.

EXAMPLE I

As a specific example of the preparation of the growth inhibiting substance of the present invention, extracts were prepared from bovine connective tissues. Bovine connective tissues which were extracted were nasal septum cartilage, scapular epiphyseal growth plate, and dermis. The tissues were minced and placed in five volumes of an extraction medium comprising a 1.0 M aqueous solution of guanadine hydrochloride, the solution having a pH of 6.0. The mixture of tissue and extraction medium was stirred for 24 hours at 5° C. The resultant aqueous extract was separated from the tissue and dialyzed exhaustively against water. The dialyzed extract was then lyophilized.

Dialyzed and lyophilzed extract from scapular epiphyseal growth plate was redissolved in 4.0 M guanidine hydrochloride solution, and dialyzed through an Amicon filter membrane with a pore size which allowed compounds of molecular weight 50,000 or below to pass through the membrane. Following dialysis, the solutions on both sides of the membrane were dialyzed exhaustively against water and lyophilized.

There were thereby obtained lyophilized extracts of bovine cartilage and of bovine dermis, as well as lyophilized extracts from bovine cartilage which had been fractionated into an extract having a molecular weight of 50,000 or below and an extract having a molecular weight higher than 50,000. These lyophilized extracts were then used to demonstrate their activity as inhibitors of cell proliferation.

EXAMPLE II

Cultures of various tissue cell types were prepared for test purposes. Bovine aortic endothelial cells were cultured from aortas collected from a local slaughter house. Fresh aortas were immediately transported to the laboratory. There, the two ends of each aorta were clamped and the branches ligated. The lumen was rinsed with about 50 ml of 0.9% NaCl. The aorta was then slightly distended with 25–50 ml of complete tissue culture medium. After about 5 minutes, the fluid was removed with a syringe and needle and 5 ml aliquots dispensed into Falcon T-25 plastic flasks. The flasks were incubated at 37° C in a humidified 5% $Co_2$-air atmosphere. The cultures generally required 8–12 days to reach confluency.

Steer fibroblasts were isolated from the subcutaneous tissue of ears from freshly slaughtered animals. Tissues were removed aseptically and incubated in a solution of 2 mg collagenase/ml HEPES. Two hours of digestion at 37° C was sufficient to yield $1 \times 10^6$ cells for planting into Falcon flasks.

Bovine embryo fibroblasts were purchased from GIBCO Corp., Grand Island, N.Y. Second passage human foreskin fibroblasts were also obtained.

The tissue culture medium used for all cell types was RPMI 1640, obtained from GIBCO Corp., Grand Island, N.Y., supplemented with 20% fetal calf serum which had been heated for 50 minutes at 56° C to inactivate bovine infectious agents present in the serum. Increased buffering capacity was provided by adding 20 mM HEPES. Antibiotics were added to yield a final concentration of gentamycin, 50 ug/ml and amphotericin B, 5 ug/ml in the complete medium. The medium was made up from the commercially supplied powder as a 2X concentrate and then passed through 0.22 u pore size millipore filters for sterilization.

When tissue extracts or other materials were to be added, the lyophilized extracts were hydrated in distilled water, sterilized by filtration, and then added to the concentrated culture medium. The filtration clarified the cloudiness seen in the aqueous solution of the extract.

For biological assays of the tissue extracts, established cultures of secondary cells were subcultured in 35 × 10 mm Falcon tissue culture dishes at an initial density of 2 × $10^4$ cells/ml in tissue culture medium and an additional 1 ml of medium added. The next day, the medium was removed and replaced with 2 ml of tissue culture medium containing the materials to be tested or with an equal volume of control medium. Control cell counts were done at this time.

The cultures were refed on the third day after test materials were added. A 2.25% solution of disodium ethylene diamine tetra-acetic acid was then prepared in Ca-Mg free phosphate buffered saline, pH 7.4. The cells were then removed from the dish by digesting with a 0.25% trypsin solution. Cell counts of the trypsin dispersed cells were done with a hemocytometer after staining with a 1% filtered solution of tripan blue. Two culture dishes were counted each day for each experimental treatment. Each set of experiments was repeated at least four times. At the termination of the experiments, some cultures were fixed in 70% methanol and stained with hematoxylin. For dose-response curve studies of cartilage-derived materials, counts were done only at the beginning of the experiment and 3 days after the test material was added. In such experiments, three dishes were counted for each dose and the experiment was repeated three times.

Since identification of endothelial cells depends in large part on the presence of Weibel-Palade bodies, electron microscopy was done on these cultured cells and these organelles were found as expected. For this, the culture dishes were washed with 0.9% NaCl. The cells were then scraped off the culture dish with a rubber spatula, fixed in 2.5% cacodylate buffered gluteraldehyde, washed overnight in buffer, stained en bloc in uranyl acetate, dehydrated and embedded in Epon 812. Sections were mounted on copper grids, stained with lead citrate and studied in an electron microscope.

The effects of the lyophilized extract of bovine cartilages on the growth of endothelial cells were determined. 40,000 endothelial cells in 2 ml of culture medium were initially dispensed into 35 mm Petri dishes. The following day the extract to be tested was injected into the dish, three dishes for each extract. Three control dishes were also provided, which were refed only with culture medium the day after culturing was begun.

Three days after injection of the respective lyophilized extracts, cell counts were done on each dish. In the case of the control dishes, the original population of 40,000 cells had increased to 70,000. Table I shows the cell counts of the dishes containing lyophilized cartilage extract at three different concentrations of lyophilized extract.

TABLE I

EFFECT OF CARTILAGE EXTRACT ON ENDOTHELIAL CELL GROWTH

| Dose, | Cells/dish |
|---|---|
| micrograms lyophilized extract per ml. of culture medium | |
| 500 | 52,000 |
| 100 | 285,000 |
| 20 | 510,000 |
| 0 | 700,000 |

It will be seen from Table I that at a dosage of 500 micrograms of lyophilized extract per milliliter of culture medium, proliferation of endothelial cells was substantially inhibited, the cell count increasing only to 52,000 from the original count of 40,000. At lower dosages, inhibition was less complete, but in each case the cell count was substantially less than the 700,000 cell count of the control after 3 days.

Similar testing was done utilizing the fraction of lyophilized cartilage extract having a molecular weight greater than 50,000. There was no observed inhibition of proliferation of endothelial cells using this fraction, the cell count at a dosage level of 500 micrograms/milliliter being 710,000 after three days, not substantially different from the cell count of 700,000 in the control.

However, the fraction of lyophilized cartilage extract having a molecular weight of 50,000 and below was substantially more potent as a growth inhibitor than the lyophilized extract which was the subject of Table I. Table II shows the results of this test, which was carried out in the same manner as testing of the unfractionated extract.

TABLE II

EFFECT OF CARTILAGE EXTRACT HAVING A MOLECULAR WEIGHT OF 50,000 AND BELOW ON ENDOTHELIAL CELL GROWTH

| Dose | Cells/dish |
|---|---|
| micrograms lyophilized extract per ml. of culture medium | |
| 500 | 22,000 |
| 100 | 65,000 |
| 20 | 260,000 |
| 5 | 300,000 |
| 0 | 700,000 |

It will be seen from Table II that the fraction of lyophilized extract having a molecular weight of 50,000 or below was effective at inhibiting proliferation of endothelial cells at dosages as low as 5 micrograms per milliliter.

The tests of which the results are reported in Tables I and II were repeated three times, and gave virtually identical results.

The same lyophilized extracts of bovine cartilage used in the tests of which the results are shown in Tables I and II were evaluated for activity in inhibiting proliferation of mature steer fibroblasts in the same culture medium. There was no significant growth inhibition, now was there significant growth inhibition of steer fibroblasts by lyophilized extracts of dermis. However, lyophilized extract from bovine cartilage was found to inhibit proliferation of fetal bovine fibroblasts. The inhibitory effect of lyophilized extract from bovine cartilage on fetal bovine fibroblasts was less marked than the inhibitory effect on bovine endothelial cells. There was also growth inhibition by extracts from bovine cartilage on infant human foreskin fibroblasts, but again the degree of inhibition was less marked than in the case of endothelial cells.

Lyophilized extracts of dermis did not inhibit growth of fetal bovine fibroblasts, although they did inhibit growth of endothelial cells as effectively as cartilage extracts. Lyophilized extracts of bovine aorta and of canine cartilage also inhibited endothelial cell growth.

The inhibitory effect of extracts from connective tissue on cell proliferation is believed to provide an explanation as to why some such tissues are relatively resistant to invasion by either neoplasms or inflammatory processes. It has been observed for many years that poorly vascularized or avascular tissues such as cartilage are relatively resistant to invasion. Clinicians and pathologist have long known, for example, that most forms of cancers of the respiratory passages often encase, but seldom invade, bronchial or laryngeal cartilages. More recently, investigation of the resistance of certain tissues to invasion by explantation on to the chick chorioallantoic membrance, showed that tissues which normally have a blood supply are rapidly invaded by vascularized mesenchyme originating from the chick embryo. On the other hand, post-natal hyaline cartilage, which is virtually devoid of blood vessels, was substantially impenetrable under the same conditions. *American Journal of Pathology,* Volume 73, No. 3 Pages 765-772, December 1973. Although applicants do not intend to be bound by theory, nor to restrict the scope of their invention by theory, it is believed that the presence of the cell proliferation inhibiting substance of the present invention at relatively high concentrations in poorly vascularized or avascular tissues such as cartilage and blood vessels is responsible for the resistance of such tissues to invasion.

EXAMPLE III

As a further specific example of the preparation of the growth inhibiting substance of the present invention, an extract was prepared from bovine cartilage utilizing an alternate extraction method. Bovine nasal septum cartilage was minced and placed in five volumes of an extraction medium comprising a 1.0 M aqueous solution of guanidine hydrochloride, the solution having a pH of 6.0. The mixture of tissue and extraction medium was stirred for 48 hours at 5° C.

The resultant aqueous extract was separated from the tissue, and guanidine hydrochloride was added to the aqueous extract in an amount sufficient to raise the concentration from 1.0 M to 3.0 M. The resultant 3.0 M aqueous extract was subjected to pressure dialysis, using a dialysis membrane which permitted passage through it of materials having a molecular weight below about 100,000. Dialysis was continued until equilibrium was attained. About 10% of the substance extracted from the tissue passed through the dialysis membrane.

The resultant dialysate comprising extracted substance having a molecular weight below about 100,000, was again subjected to pressure dialysis, using a membrane which permitted passage through it of materials having a molecular weight of below about 50,000. The resultant dialysate was collected and dialysed exhaustively against water through a membrane to deplete it of guanidine hydrochloride and other substances having a molecular weight below about 3,500. The dialyzed extract was lyophilized to provide a substance which also had activity as an inhibitor of cell proliferation.

Thus, there has been provided a composition of matter having activity as an inhibitor of cell proliferation, and there has also been provided methods of preparing such a composition and methods of inhibiting cell proliferation utilizing such a composition.

Various of the features of the present invention are set forth in the following claims.

What is claimed is:

1. The method of preparing a composition of matter having activity as an inhibitor of cell proliferation comprising the steps of providing connective tissue having a high content of collagen or proteoglycans in condition for extraction, extracting said inhibitor from said tissue with an aqueous extraction medium which includes a solute which does not irreversibly denature the proteinaceous matter to be extracted, separating the resultant aqueous extract from the tissue, recovering from the aqueous extract substances having a molecular weight below about 50,000, treating the fraction of aqueous extract having a molecular weight below about 50,000 to remove salts therefrom, and dehydrating the resultant material.

2. The method of claim 1 wherein the connective tissue comprises tissue normally devoid of an intimate capillary blood supply.

3. The method of claim 2 wherein the tissue comprises cartilage.

4. The method of claim 2 wherein the tissue comprises blood vessels.

5. A composition of matter having activity as an inhibitor of cell proliferation comprising the product of the method of claim 1.

6. A composition of matter having activity as an inhibitor of cell proliferation comprising the product of the method of claim 2.

7. A method of inhibiting proliferation of cells comprising treating the cells with the product of claim 1.

8. A method of inhibiting proliferation of cells comprising treating the cells with the product of claim 2.

9. A method of inhibiting proliferation of cells comprising treating the cells with the product of claim 3.

10. A method of inhibiting proliferation of cells comprising treating the cells with the product of claim 4.

* * * * *

UNITED STATES PATENT AND TRADEMARK OFFICE
CERTIFICATE OF CORRECTION

PATENT NO. : 4,042,457

DATED : August 16, 1977

INVENTOR(S) : Klaus E. Kuettner et al.

It is certified that error appears in the above-identified patent and that said Letters Patent are hereby corrected as shown below:

Column 1, line 1, before "The" insert --The invention described herein was made in the course of work under a grant or award from the Department of Health, Education, and Welfare.--.

Column 2, line 30, "lyophilzed" should be --lyophilized--.
Column 4, line 4, "70,000" should be --700,000--.
Column 5, line 27, "membrance" should be --membrane--.

Signed and Sealed this

Seventh Day of March 1978

[SEAL]

Attest:

RUTH C. MASON
Attesting Officer

LUTRELLE F. PARKER
Acting Commissioner of Patents and Trademarks